United States Patent [19]

Lundquist et al.

[11] Patent Number: 5,475,154
[45] Date of Patent: Dec. 12, 1995

[54] METHOD FOR PRODUCING HIGH-PURITY BISPHENOLS

[75] Inventors: Eric G. Lundquist, North Wales; Michael P. Bigwood, Oreland, both of Pa.

[73] Assignee: Rohm and Haas Company, Philadelphia, Pa.

[21] Appl. No.: 209,574

[22] Filed: Mar. 10, 1994

[51] Int. Cl.$^6$ ............................ C07C 39/12; C07C 39/16
[52] U.S. Cl. ...................... 568/727; 568/723; 568/724; 568/729
[58] Field of Search .................................. 568/724, 729, 568/723, 727

[56] References Cited

U.S. PATENT DOCUMENTS

| | | | |
|---|---|---|---|
| 4,766,254 | 8/1988 | Faler et al. | |
| 5,008,470 | 4/1991 | Powell et al. | 568/724 |
| 5,059,721 | 10/1991 | Powell et al. | |
| 5,124,490 | 6/1992 | Cipullo | 568/724 |
| 5,233,096 | 8/1993 | Lundquist et al. | |
| 5,288,926 | 2/1994 | Patrascu et al. | 568/723 |

FOREIGN PATENT DOCUMENTS

| | | |
|---|---|---|
| 1863 | 5/1979 | European Pat. Off. . |
| 329075 | 8/1989 | European Pat. Off. . |
| 1377227 | 12/1974 | United Kingdom . |

*Primary Examiner*—Alan Siegel
*Attorney, Agent, or Firm*—John E. Taylor, III

[57] ABSTRACT

Low-color bisphenols may be produced by condensing phenol with ketones in the presence of a strong-acid cation exchange resin acting as an acid catalyst for the condensation reaction, and of a small amount, relative to the acid catalyst, of a weak-base anion exchange resin.

21 Claims, No Drawings

1

METHOD FOR PRODUCING HIGH-PURITY BISPHENOLS

This invention relates to a method for making bisphenols, and more particularly to a condensation reaction between phenol and aliphatic aldehydes or ketones in the presence of cation exchange resins to prepare bisphenols.

BACKGROUND OF THE INVENTION

Bisphenols such as 2,2-bis(4'-oxyphenylpropane), or bisphenol-A, and 2,2-bis(4-hydroxyphenyl)butane, or bisphenol-B, are made by a condensation reaction of phenol with ketones, as for example with acetone for bisphenol-A, or with methyl ethyl ketone for bisphenol-B. Similar condensation reactions occur between phenol and aldehydes. Such condensation reactions are acid catalyzed, and particularly advantageous acid catalysts for the reactions are strong-acid cation exchange resins which carry the anionic portion of the acid on a solid substrate, allowing its easy removal at the completion of the reaction.

A particular problem with making bisphenol-A using cation exchange resins as the acid catalyst is that the crude bisphenol-A product may be strongly colored, and this color, unless removed, carries through into products, such as fibers, transparent sheet for glazing and the like, made from the bisphenol-A and having particularly stringent requirements for low color.

Impurities, particularly those such as sulfonic acid residues which lead to decomposition during distillation, have been removed from bisphenol-A by treating the crude bisphenol-A with anion exchange resins prior to its distillation (Faler et al., U.S. Pat. No. 4,766,254), but this treatment is a separate step from the reaction which produces the crude bisphenol-A. It would be highly advantageous to produce bisphenols such as bisphenol-A with low color directly from the condensation reaction.

SUMMARY OF THE INVENTION

We have discovered a method for producing bisphenols having low color which comprises reacting phenol with an aliphatic aldehyde or ketone at an elevated temperature, in the presence of a catalytic amount of strong-acid cation exchange resin in the hydrogen form, and from about 0.5% to about 15% by weight, based on the weight of the cation exchange resin, of a weak-base anion exchange resin.

DETAILED DESCRIPTION OF THE INVENTION

Although the process of the present invention may be applied generally to acid-catalyzed condensation reactions employing cation-exchange resins as the catalyst, it is particularly advantageous in those condensation reactions where the product must have a low color, as for example the reaction of phenol with acetone to make bisphenol-A.

The acid catalysts useful in the process of the present invention are strong-acid cation exchange resins, and preferably those strong-acid cation exchange resins having sulfonate functionality. Preferred polymers from which the acid catalysts are made are crosslinked aromatic copolymers, such as copolymers of ethylvinylbenzene, styrene, α-methylstyrene, vinyltoluene, vinylnaphthalene and the like with a polyvinyl-unsaturated crosslinking monomer which may be aliphatic, such as ethylene glycol diacrylate, ethylene glycol dimethacrylate, trimethylolpropane di- and triacrylates, trimethylolpropane di- and trimethacrylates, divinylketone, allyl acrylate, diallyl maleate, diallyl fumarate, diallyl succinate, diallyl carbonate, diallyl malonate, diallyl oxalate, diallyl adipate, diallyl sebacate, divinyl sebacate, N,N'-methylenedimethacrylamide, N,N'-methylenediacrylamide and polyvinyl or polyallyl ethers of glycol, of glycerol, of pentaerythritol, of mono- or dithio- derivatives of glycols or resorcinol and the like, or aromatic, such as divinylbenzene, trivinylbenzene, divinyltoluenes, divinylnaphthalenes, diallyl phthalate, divinylxylene, divinylethylbenzene and the like, or a heterocyclic crosslinker such as divinylpyridine, or mixtures of any of the above. Also preferred are copolymers with a relatively low level of crosslinking, such as those prepared with from about 0.05% to about 10%, by weight, of a crosslinking monomer, based on the total weight of monomers. Especially preferred are copolymers of styrene with divinylbenzene as a crosslinking monomer, and functionalized with sulfonic acid functional groups. The polymers may be made by bulk, emulsion or suspension polymerization, or other polymerization techniques known to those having ordinary skill in the art. Preferred is suspension polymerization, which produces spherical polymer particles, or beads, of copolymer More preferred polymers are gel beads of copolymer, that is, beads containing only micropores or pores of about 50 Ångstrom units (Å) or smaller in diameter, although macroporous copolymer beads, such as those produced by suspension polymerization in the presence of a porogen which acts as a solvent for the monomer but a non-solvent for the polymer, those produced by copolymerization in the presence of a non-crosslinked, soluble polymer such as polystyrene, which may subsequently be dissolved, leaving macropores, and those produced by other methods known to those of ordinary skill in the art for generating macropores, may be used. These polymers may be functionalized with strong-acid functional groups according to processes known to those having ordinary skill in the art, as for example, sulfonation with concentrated sulfuric acid, fuming sulfuric acid or chlorosulfonic acid. One method of making acid catalysts useful in the present invention is disclosed by Lundquist in U.S. Pat. No. 5,233,096.

The weak-base anion exchange resin useful in the process of the present invention is a crosslinked, synthetic polymer of a monoethylenically unsaturated monomer, functionalized with a primary or secondary amine functional group. As with the acid catalyst, the polymers for the weak-base anion exchange resin may be made by bulk, emulsion or suspension polymerization, or other polymerization techniques known to those having ordinary skill in the art. The polymer is preferably in the form of a bead having a diameter of from about 10 μm to about 2 mm, preferably from about 20 μm to about 1 mm. These beads may be produced by suspension polymerization. The copolymer may be made as gel beads or as macroporous beads, as for example by the methods described above for producing macroporous copolymers useful for preparing the catalyst resins.

The crosslinking level is at least sufficient to render the polymer insoluble in water and organic solvents. Crosslinking is preferably achieved by copolymerizing the monoethylenically unsaturated monomer with a polyethylenically unsaturated monomer, which may be aliphatic, such as ethylene glycol diacrylate, ethylene glycol dimethacrylate, trimethylolpropane di- and triacrylates, trimethylolpropane di- and trimethacrylates, divinylketone, allyl acrylate, diallyl maleate, diallyl fumarate, diallyl succinate, diallyl carbonate, diallyl malonate, diallyl oxalate, diallyl adipate, diallyl sebacate, divinyl sebacate, N,N'-methylenedimethacrylamide, N,N'-methylenediacrylamide and polyvinyl or polyallyl ethers of glycol, of glycerol, of pentaerythritol, of mono- or dithio- derivatives of glycols or resorcinol and the like, or aromatic, such as divinylbenzene, trivinylbenzene, divinyltoluenes, divinylnaphthalenes, diallyl phthalate, divinylxylene, divinylethylbenzene and the like, or heterocyclic crosslinkers such as divinylpyridine, or mixtures of any of the above. Preferred is divinylbenzene. This polyethylenically unsaturated monomer acts as a crosslinking monomer. The level of crosslinking monomer is preferably from about 0.5% to about 60%, preferably from about 1% to about 20%, by weight, of the total monomers.

The monoethylenically unsaturated monomer may be an acrylic monomer such as acrylic or methacrylic acid or their esters, including esters of $C_1$-$C_{18}$ alkyl, cycloalkyl, aryl, aralkyl and alkaryl alcohols, acrylonitrile, methacrylonitrile, vinyl chloride, vinyl formate, vinyl alkyl ethers such as methylvinyl ether, acrylamide, methacrylamide, or it may be an aromatic monomer such as ethylvinylbenzene, styrene, α-methylstyrene, vinyltoluene, vinylnaphthalene and the like, or mixtures of any of the above. Preferred is styrene.

The crosslinked copolymer is functionalized with a primary or secondary amine group as the weak-base anion-exchange group. The amine group may be introduced as a group on one or more of the monomers which are polymerized to form the copolymer, or it may be introduced into the copolymer subsequent to polymerization through processes which are well known to those having ordinary skill in the art, as by first introducing halomethyl groups, preferably chloromethyl groups, into the copolymer and subsequently aminating the introduced halomethyl groups with a primary or secondary amine. Alternatively, a halomethyl-group-containing monomer may be used as one of the monomers from which the copolymer is prepared, and the halomethyl groups in the copolymer may then be aminated directly. The level of weak-base functionality may be from about 0.1 to about 6 milliequivalents per gram (meq/g) of dry resin, and preferably from about 2 to about 6 meq/g.

While resins in which styrene is the monoethylenically unsaturated monomer are preferred, weak-base resins useful in the present invention may also be acrylic resins, as indicated by the list of usable monomers above. These may be prepared by copolymerizing an acrylic or methacrylic ester with a crosslinking monomer such as divinylbenzene to form an insoluble copolymer which is then functionalized with an amine containing at least one primary amine group and one secondary or tertiary amine group, preferably a tertiary amine group. The primary amine group reacts with the polyester to form an amide, and the secondary or tertiary amine group forms the active weak-base anion-exchange site.

Weak-base phenolic resins may also be used in the process of the present invention. These resins may be prepared by condensing phenol with formaldehyde in the presence of an amine. Other resins which may be used in the present process are weak-base poly(vinylpyridine) resins; these resins may be prepared by copolymerizing vinylpyridine with a crosslinking monomer such as divinylbenzene.

Without wishing to be bound by theory, we believe that the basicity of the weak-base anion exchange resin directly affects the effectiveness of the resin in removing color from the products of the condensation reaction; that is, the more basic the resin, the more effectively it removes the color. This is supported by the results shown in the Examples below, in which the color of the resulting bisphenol-A is lowest with the most basic resins, those of Examples 1 and 2, and is intermediate with the less basic resin of Example 3. The color of the bisphenol-A produced in Example 4, with the least basic resin, is improved over that where no weak-base resin is used, but the improvement is much less than that observed with the more basic weak-base resins. Consequently, the preferred resins are those which are more strongly basic. The less preferred resins, that is, those which are less basic and consequently less effective at removing the color, may be chosen for a particular application because of other properties, as for example physical parameters such as thermal stability or longer useful lifetime in a particular application.

The condensation reaction of the present invention, between phenol and the aldehyde or ketone, is carried out at elevated temperature in the presence of the acid catalyst and the weak-base anion exchange resin. The acid catalyst is preferably present in amounts from about 10% to about 200%, by weight, of the total liquid amount, including the reactants, solvents and diluents, and the weak-base anion exchange resin is preferably present in amounts from about 0.5% to about 15% of the weight of the acid catalyst, more preferably from about 1 to about 10%, and still more preferably from about 3 to about 8%. The temperatures useful for the reaction range from about 30° C. to about 90° C., preferably from about 60° C. to about 80° C. Above about 90° C. the weak-base resins useful in the present invention have a limited useful life because of thermal instability, and below about 30° C. the reaction will not occur rapidly enough to be practical. Preferred in the reaction is the use of a ketone to condense with the phenol; more preferred is a $C_1$-$C_4$ ketone, that is, a ketone having two alkyl groups, each of which has from one to four carbon atoms. Still more preferred is a ketone selected from acetone and methyl ethyl ketone, and particularly preferred is acetone as the ketone.

In a preferred embodiment of the present invention, the acid catalyst is in the physical form of beads contained in a vessel, the beads forming a bed of the catalyst, and the weak-base anion exchange resin, also in bead form, is mixed throughout the bed. A heated liquid stream containing phenol and ketone, preferably acetone or methyl ethyl ketone, is brought into contact with the catalyst bed for a sufficient time for the condensation reaction between the phenol and the ketone to occur, the liquid stream, containing the reaction products and any unreacted phenol and ketone which may be present, is separated from the catalyst bed, and bisphenol is recovered from the liquid stream. One having ordinary skill in the art will be able to choose appropriate conditions, such as a batch operation, e.g., in which the bed is loaded with the liquid stream, and the liquid stream is removed from the bed after the desired reaction has occurred, or the more preferred continuous operation, e.g., in which the liquid stream is fed continuously into one end of the bed and caused to pass through it at a rate which permits sufficient time in the bed for the reaction to occur, with the liquid stream being removed continuously from the other end of the bed. Similarly, the reaction equipment, the choice of upflow or downflow for the direction of passage of the liquid stream through the bed, the reaction time and temperature, the particular reactants, and the method of recovering the bisphenol, e.g., crystallization or distillation, are easily selected based upon the guidance provided herein and the knowledge available to one having ordinary skill in the art.

The following examples are intended to illustrate the present invention and not to limit it except as it is limited in the claims. All reagents used are of good commercial quality unless otherwise indicated, and all percentages and ratios given herein are by weight unless otherwise indicated.

EXAMPLE 1

This example illustrates the process of the present invention as embodied by the formation of low-color bisphenol-A from phenol and acetone in the presence of a strong-acid polymeric catalyst and a weak-base anion exchange resin.

To a flask containing 90 g of phenol (purity greater than 99%) was added 10 g (10% by weight) of dried, styrenic cation exchange resin crosslinked with 4% divinylbenzene and functionalized with 4.95 meq/g of sulfonic acid groups (dry basis) and 0.2 g of dried styrenic anion exchange resin crosslinked with 8% divinylbenzene and functionalized with 4.8 meq/g of dimethylaminobenzyl groups (dry basis). The flask contents were heated to 75° C. and held at that temperature, with stirring, for one hour. A 10-ml charge of acetone was added and stirring was continued at 75° C. as the progress of the reaction was monitored by removing 1-ml samples, quenching them in a methanol-water mixture, and determining the composition of the reaction mixture by liquid chromatography. Acetone conversion was calculated, from the relative peak areas of the liquid chromatograms, to be the bisphenol-A total peak area (including ortho and para isomers) as a percentage of the total area of the acetone peak and the bisphenol-A product peaks. The conversion for this reaction was 72%. Selectivity was calculated from the liquid chromatogram to be the area of the bisphenol-A peaks as a percentage of the total area of all peaks produced by reaction products of phenol and acetone. The selectivity of this reaction was 86%.

The final reaction mixture, containing acetone, bisphenol-A, phenol and bisphenol-A byproducts, was dissolved with an equal volume of methanol and transferred to a quartz spectrophotometer cell. The optical absorbance of the mixture was measured at 455 nm against a platinum-cobalt color standard, and the mixture was calculated to have an APHA color of 8.

EXAMPLE 2

This example is intended to illustrate the present invention using a different weak-base resin, functionalized with dimethylpropylamino groups.

Example 1 was repeated, using an acrylic copolymer crosslinked with 6% divinylbenzene and functionalized with 4.8 meq/g of dimethylpropylamino groups as the weak-base anion exchange resin, to produce a final reaction mixture having an APHA color of 6.

EXAMPLE 3

This example is intended to illustrate the process of the present invention using yet another weak-base resin, a phenol-formaldehyde condensation resin functionalized with mixed amines.

Example 1 was repeated, using a phenol-formaldehyde condensation resin functionalized with 3.8 meq/g of a mixture of primary, secondary and tertiary amines. The final reaction mixture had an APHA color of 16.

EXAMPLE 4

This example is intended to illustrate the process of the present invention using yet another weak-base resin, a vinylpyridine resin in which the monomer itself is the source of the weak-base functional groups.

Example 1 was repeated using a vinylpyridine resin crosslinked with 20% divinylbenzene and having 5.1 meq/g of weak-base groups from the vinylpyridine, as the weak-base resin. The final reaction mixture had an APHA color of 37.

EXAMPLE 5

This comparative example is intended to illustrate the results when phenol and acetone are reacted in the presence of a strong-acid catalyst and in the absence of the weak-base resin.

Example 1 was repeated, using the styrene-4% divinylbenzene copolymer functionalized with 4.95 meq/g (dry basis) of sulfonic acid functional groups, but omitting the weak-base anion exchange resin. The final reaction mixture had an APHA color of 47. The conversion, as defined in Example 1, for the reaction was 73%, and the selectivity, also defined in Example 1, of the reaction was 85%.

We claim:

1. A method for producing bisphenols having low color which comprises reacting phenol with an aliphatic aldehyde or ketone at an elevated temperature, in the presence of a catalytic amount of strong-acid cation exchange resin in the hydrogen form, and from about 0.5% to about 15% by weight, based on the weight of the cation exchange resin which is a crosslinked, synthetic polymer of a monoethylenically unsaturated monomer, functionalized with a primary or secondary amine functional group, of a weak-base anion exchange resin.

2. The method of claim 1 wherein the aliphatic aldehyde or ketone is a $C_1$–$C_4$ ketone.

3. The method of claim 1 where the aliphatic aldehyde or ketone is selected from the group consisting of acetone and methyl ethyl ketone.

4. The method of claim 2 wherein the weak-base anion exchange resin is in the form of anion exchange resin beads having a diameter from about 10 μm to about 2 mm.

5. The method of claim 4 wherein the anion exchange resin beads have a diameter of from about 20 μm to about 1 mm.

6. The method of claim 4 wherein the anion exchange resin beads are gel beads.

7. The method of claim 4 wherein the anion exchange resin beads are macroporous beads.

8. The method of claim 4 wherein the anion exchange resin beads are phenolic anion exchange resin beads.

9. The method of claim 4 wherein the anion exchange resin beads are anion-exchange-functionalized, crosslinked copolymer beads prepared from a monomer mixture containing from about 1 to about 20%, based on the total weight of the monomers, of a crosslinking monomer.

10. The method of claim 9 wherein the copolymer beads are styrenic copolymer beads.

11. The method of claim 9 wherein the copolymer beads are acrylic copolymer beads.

12. The method of claim 1 wherein the weak-base anion exchange resin has a level of weak-base functionality of from about 0.1 to about 6 milliequivalents per gram of dry resin.

13. The method of claim 2 wherein the weak-base anion exchange resin has a level of weak-base functionality of from about 2 to about 6 milliequivalents per gram of dry resin.

14. The method of claim 2 wherein the cation exchange resin is present at from about 10% to about 200%, by weight, based on the total liquid weight.

15. The method of claim 14 wherein the weak-base anion exchange resin is present at front about 1% to about 10%, by weight, of the cation exchange resin.

16. The method of claim 14 wherein the weak-base anion exchange resin is present at front about 3% to about 8%, by weight, of the cation exchange resin.

17. The method of claim 15 wherein the phenol and ketone react at a temperature of front about 30° C. to about 90° C.

18. The method of claim 15 wherein the phenol and ketone react at a temperature of from about 60° C. to about 80° C.

19. The method of claim 15 wherein the cation exchange resin and anion exchange resin form a mixed bed in a vessel.

20. The method of claim 15 wherein the cation exchange resin is a cation exchange functionalized, crosslinked copolymer prepared with front about 0.5% to about 10%, based on the total monomer weight, of crosslinking monomer.

21. A method for producing bisphenol-A having low color which comprises contacting, at a temperature of from about 30° C. to about 90° C., a liquid stream containing phenol and acetone with a mixed bed of strong-acid cation exchange resin and front about 1% to about 10% by weight, based on the weight of the cation exchange resin, of a weak-base anion exchange resin which is a crosslinked, synthetic polymer of a monoethylenically unsaturated monomer, functionalized with a primary or secondary amine functional group for a sufficient time for a condensation reaction between the phenol and the acetone to occur, subsequently separating the liquid stream front the mixed bed of resins, and recovering bisphenol-A from the separated liquid stream.

* * * * *